United States Patent [19]

Müller-Gliemann et al.

[11] Patent Number: 5,376,671

[45] Date of Patent: * Dec. 27, 1994

[54] PROPENOYL-IMIDAZOLE DERIVATIVES

[75] Inventors: Matthias Müller-Gliemann, Solingen-Ohligs; Jürgen Dressel; Peter Fey, both of Wuppertal; Rudolf Hanko, Desseldorf; Walter Hübsch, Wuppertal; Thomas Krämer, Wuppertal; Ulrich Müller, Wuppertal; Martin Beuck, Erkrath; Stanislav Kazda, Wuppertal; Andreas Knorr, Erkrath; Johannes-Peter Stasch, Wuppertal; Stefan Wohlfeil, Hilden, all of Germany

[73] Assignee: Bayer Aktiengesellschaft, Leverkusen, Germany

[*] Notice: The portion of the term of this patent subsequent to Jul. 5, 2005 has been disclaimed.

[21] Appl. No.: 43,779

[22] Filed: Apr. 6, 1993

[30] Foreign Application Priority Data

Apr. 16, 1992 [DE] Germany .................. 4212796

[51] Int. Cl.⁵ .................. A61K 31/415; C07D 233/68; C07D 233/64
[52] U.S. Cl. .................. 514/399; 548/338.1; 548/340.1; 548/341.5
[58] Field of Search .............. 548/338.1, 340.1, 341.5; 514/399

[56] References Cited

U.S. PATENT DOCUMENTS

| 4,355,040 | 10/1982 | Furukawa, et al. | 424/273 R |
| 4,946,841 | 8/1990 | Baader, et al. | 514/247 |
| 5,191,086 | 3/1993 | Ross | 548/341.5 |

FOREIGN PATENT DOCUMENTS

| 403158 | 6/1990 | European Pat. Off. . |
| 0399731 | 11/1990 | European Pat. Off. . |
| 0399732 | 11/1990 | European Pat. Off. . |
| 0403158 | 12/1990 | European Pat. Off. . |
| 0403159 | 12/1990 | European Pat. Off. . |
| 0407102 | 1/1991 | European Pat. Off. . |
| 0425211 | 5/1991 | European Pat. Off. . |
| 9100281 | 1/1991 | WIPO . |

OTHER PUBLICATIONS

Journal of Medicinal Chemistry, Bd. 35, Nr. 21, Oct. 16, 1992, pp. 3858–3872, Keenan R. M., et al.
Journal of Medicinal Chemistry, Bd. 34, Nr. 4, Apr. 4, 1991, pp. 1514–1517, Weinstock J. et al.
Journal of Medicinal Chemistry, Bd. 33, Nr. 5, May 1990, pp. 1312–1329, Duncia J. V. et al.
S. R. Adapa & C. S. N. Prasad, J. Chem. Soc., Perkin Trans. 1, (9) pp. 1706–1707 (1989).
J. C. Sheehan, S. L. Ledis, J. Am. Chem. Soc 95, 875–879 (1973).
Frerman et al., J. Biol. Chem. 258, 7087–7093 (1983).
N. L. Benoiton, K. Kluroda, Int. Pept. Prot. Res. 17, 197–204 (1981).
R. Ross, J. Cell. Biol. 50, 172–186 (1971).
N. Bartlett, et al., J. Chem. Soc., Chem. Commun., (2), 167–168 (1966).

*Primary Examiner*—Patricia L. Morris
*Attorney, Agent, or Firm*—Sprung Horn Kramer & Woods

[57] ABSTRACT

Propenoyl-imidazole derivatives are prepared by reaction of appropriate imidazoylaldehydes with CH-acidic compounds and subsequent dehydration of the intermediates. The propenoyl-imidazole derivatives can be employed as active compounds in medicaments for the treatment of arterial hypertension and atherosclerosis.

11 Claims, No Drawings

PROPENOYL-IMIDAZOLE DERIVATIVES

The invention relates to propenoyl-imidazole derivatives, a process for their preparation and their use in medicaments, in particular as hypotensive and antiatherosclerotic agents.

It is known that renin, a proteolytic enzyme, eliminates the decapeptide angiotensin I from angiotensinogen in vivo, and angiotensin I in turn is broken down in the lung, the kidneys or other tissues to give the hypertensive octapeptide angiotensin II. The various effects of angiotensin II, such as, for example, vasoconstriction, $Na^+$ retention in the kidney, release of aldosterone in the adrenal gland and an increase in tone of the sympathetic nervous system, act synergistically in the sense of a blood pressure increase.

Moreover, angiotensin II has the property of promoting the growth and replication of cells such as, for example, cardiac muscle cells and smooth muscle cells, these growing and proliferating to an increased extent in various disease states (for example hypertension, atherosclerosis and cardiac insufficiency).

A possible starting point for intervention in the reninangiotensin system (RAS) is, in addition to the inhibition of renin activity, the inhibition of the activity of angiotensin-converting enzyme (ACE) and the blockade of angiotensin II receptors.

The invention relates to propenoyl-imidazole derivatives of the general formula (I)

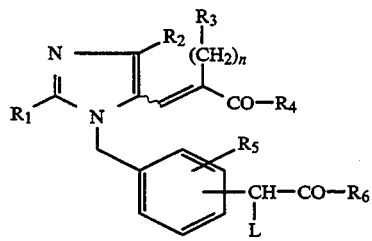

in which
- $R^1$ represents straight-chain or branched alkyl or alkenyl, each having up to 8 carbon atoms, or represents cycloalkyl having 3 to 8 carbon atoms,
- $R^2$ represents hydrogen, halogen or perfluoroalkyl having up to 5 carbon atoms,
- n represents a number 0, 1, 2 or 3,
- $R^3$ represents cycloalkyl having 3 to 7 carbon atoms,
- $R^4$ represents hydroxyl, or straight-chain or branched alkoxy having up to 6 carbon atoms, or represents a radical of the formula $—CO—NR^7R^8$,
  in which
  $R^7$ and $R^8$ are identical or different and denote hydrogen, straight-chain or branched alkyl having up to 6 carbon atoms or phenyl,
- $R^5$ represents hydrogen, halogen, nitro, hydroxyl, trifluoromethyl, trifluoromethoxy, straight-chain or branched alkyl, alkoxy or alkoxycarbonyl, each having up to 6 carbon atoms, cyano or carboxyl,
- L represents cycloalkyl having 3 to 7 carbon atoms, or represents straight-chain or branched alkyl having up to 8 carbon atoms, which is optionally substituted by phenyl,
- $R^6$ represents hydroxyl or straight-chain or branched alkoxy having up to 6 carbon atoms, or represents a radical of the formula $—NR^9SO_2R^{10}$ or

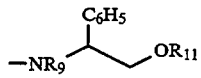

in which
- $R^9$ denotes hydrogen or straight-chain or branched alkyl having up to 4 carbon atoms,
- $R^{10}$ denotes straight-chain or branched alkyl having up to 6 carbon atoms or phenyl which is optionally substituted by straight-chain or branched alkyl having up to 6 carbon atoms,
- $R^{11}$ denotes hydrogen, straight-chain or branched alkyl having up to 6 carbon atoms or a hydroxyl-protective group and their salts.

The compounds of the general formula (I) according to the invention can also be present in the form of their salts. In general, salts with organic or inorganic bases or acids may be mentioned here.

In the context of the present invention, physiologically acceptable salts are preferred. Physiologically acceptable salts of the propenoyl-imidazole derivatives can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can also be metal or ammonium salts of the compounds according to the invention which have a free carboxyl group. Particularly preferred salts are, for example, sodium, potassium, magnesium or calcium salts and also ammonium salts which are derived from ammonia or organic amines such as, for example, ethylamine, di- or triethylamine, di- or triethanolamine, dicyclohexylamine, dimethylaminoethanol, arginine, lysine or ethylenediamine.

The compounds according to the invention can exist in stereoisomeric forms, which behave either as image and mirror-image (enantiomers) or which do not behave as image and mirror-image (diastereomers). The invention relates both to the enantiomers or diastereomers and to their respective mixtures. Like the diastereomers, the racemic forms can also be separated in a known manner into the stereoisomerically uniform constituents [cf. E. L. Eliel, Stereochemistry of Carbon Compounds, McGraw Hill, 1962].

Preferred compounds of the general formula (I) are those in which
- $R^1$ represents straight-chain or branched alkyl or alkenyl each having up to 6 carbon atoms, or represents cyclopropyl, cyclobutyl, cyclopentyl, cyclohexyl or cycloheptyl,
- $R^2$ represents hydrogen, fluorine, chlorine, bromine or perfluoroalkyl having up to 4 carbon atoms,
- n represents a number 0, 1 or 2,
- $R^3$ represents cyclopropyl, cyclobutyl, cyclopentyl, cyclohexyl or cycloheptyl,
- $R^4$ represents hydroxyl, straight-chain or branched alkoxy having up to 4 carbon atoms, or represents the group of the formula $—CO—NR^6R^8$,
  in which R⁷ and R⁸ are identical or different and denote hydrogen, straight-chain or branched alkyl having up to 4 carbon atoms or phenyl, R⁵ represents hydrogen, fluorine, chlorine, bromine, trifluoromethyl, carboxyl or straight-chain or branched alkyl, alkoxy or alkoxycarbonyl each having up to 4 carbon atoms, L represents cyclopropyl, cyclobutyl, cyclopentyl, cyclohexyl or cycloheptyl, or represents straight-chain or branched alkyl having up to 6 carbon atoms or benzyl, R⁶ represents hydroxyl or straight-chain or branched alkoxy having up to 4 carbon atoms, or represents a radical of the formula —NR⁹SO₂R¹⁰ or

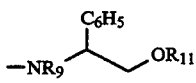

in which

R⁹ denotes hydrogen, methyl or ethyl,

R¹⁰ denotes straight-chain or branched alkyl having up to 4 carbon atoms or phenyl which is optionally substituted by straight-chain or branched alkyl having up to 4 carbon atoms, R¹¹ denotes hydrogen, straight-chain or branched alkyl having up to 4 carbon atoms, acetyl or benzyl, and their salts.

Particularly preferred compounds of the general formula (I) are those in which

R¹ represents straight-chain or branched alkyl or alkenyl, each having up to 4 carbon atoms, or represents cyclopropyl, cyclopentyl or cyclohexyl, R² represents hydrogen, fluorine, chlorine or perfluoroalkyl having up to 2 carbon atoms, n represents the number 0 or 1, R³ represents cyclopentyl or cyclohexyl, R⁴ represents hydroxyl, methoxy, ethoxy or tert-butoxy, R⁵ represents hydrogen, fluorine, chlorine, bromine, trifluoromethyl, trifluoromethoxy or methyl, L represents cyclopentyl, cyclohexyl or cycloheptyl, or represents straight-chain or branched alkyl having up to 4 carbon atoms or benzyl, R⁶ represents hydroxyl or straight-chain or branched alkoxy having up to 4 carbon atoms, or represents a radical of the formula —NR⁹SO₂R¹⁰ or

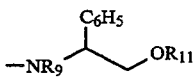

in which

R⁹ denotes hydrogen or methyl,

R¹⁰ denotes methyl or p-tolyl,

R¹¹ denotes hydrogen or straight-chain or branched alkyl having up to 3 carbon atoms or benzyl, and their salts.

Very particularly preferred compounds of the general formula (I) according to the invention are those in which the radical —CH(L)—CO—R⁶ is in the para-position to the imidazolylmethyl group.

Additionally, a process for the preparation of the compounds of the general formula (I) according to the invention has been found, characterised in that aldehydes of the general formula (II)

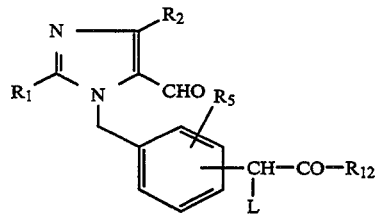

in which

R¹, R², R⁵ and L have the abovementioned meaning and

R¹² represents C₁-C₄-alkoxy, are converted by reaction with compounds of the general formula (III)

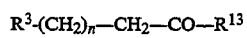

$$R^3\text{-}(CH_2)_n\text{---}CH_2\text{---}CO\text{---}R^{13}$$ (III)

in which

R³ and n have the abovementioned meaning and

R¹³ has the abovementioned meaning of R⁴ but does not represent hydroxyl, in inert solvents, in the presence of a base, to the hydroxy compounds of the general formula (IV)

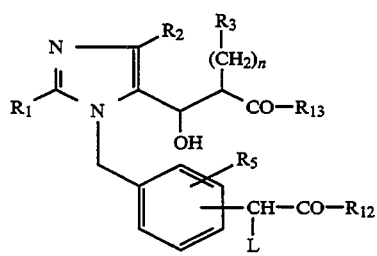

in which

R¹, R², R³, R⁵, R¹², R¹³, n and L have the abovementioned meaning, then the free hydroxyl function is blocked by introduction of a protective group, in a last step an elimination is carried out in inert solvents, in the presence of a base, if appropriate the E/Z isomers are separated, and in the case of the acids (R⁴=OH), the esters are hydrolysed, and in the case of the amides or sulphonamides, if appropriate after activation of the carboxylic acid (R¹²=OH), an amidation or sulphoamidation according to customary methods is added, in the case in which R⁹ does not represent hydrogen, the NH function is alkylated, and if appropriate the substituents R¹ and R² are introduced by customary methods, for example by reduction, oxidation, alkylation or hydrolysis or converted into other groups and if appropriate the stereoisomers are separated, and in the case of the preparation of the salts reacted with an appropriate base or acid.

The process according to the invention can be illustrated by way of example by the following reaction scheme:

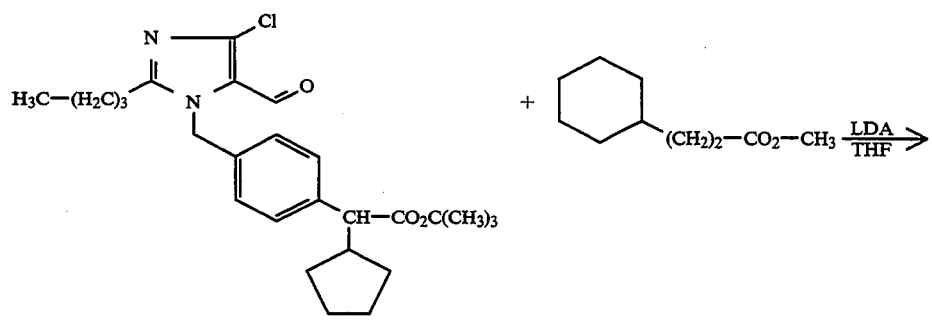
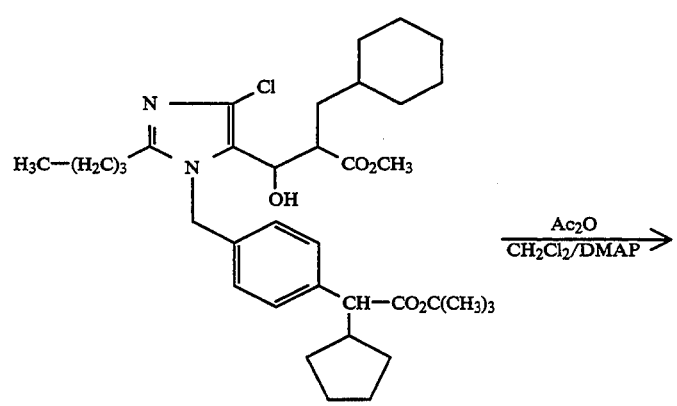
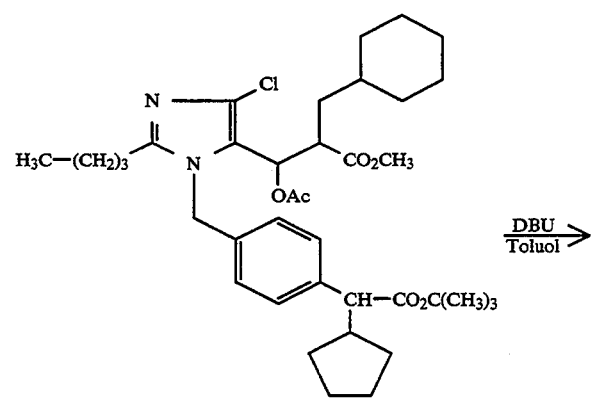
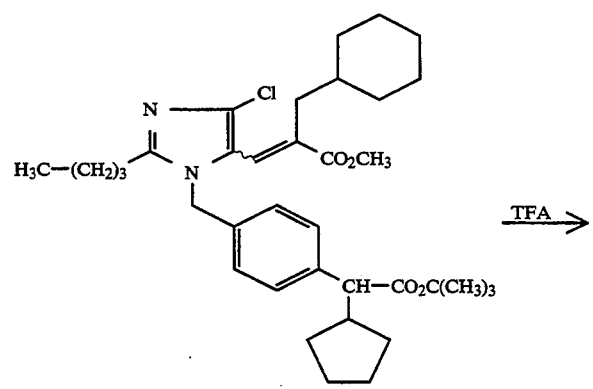

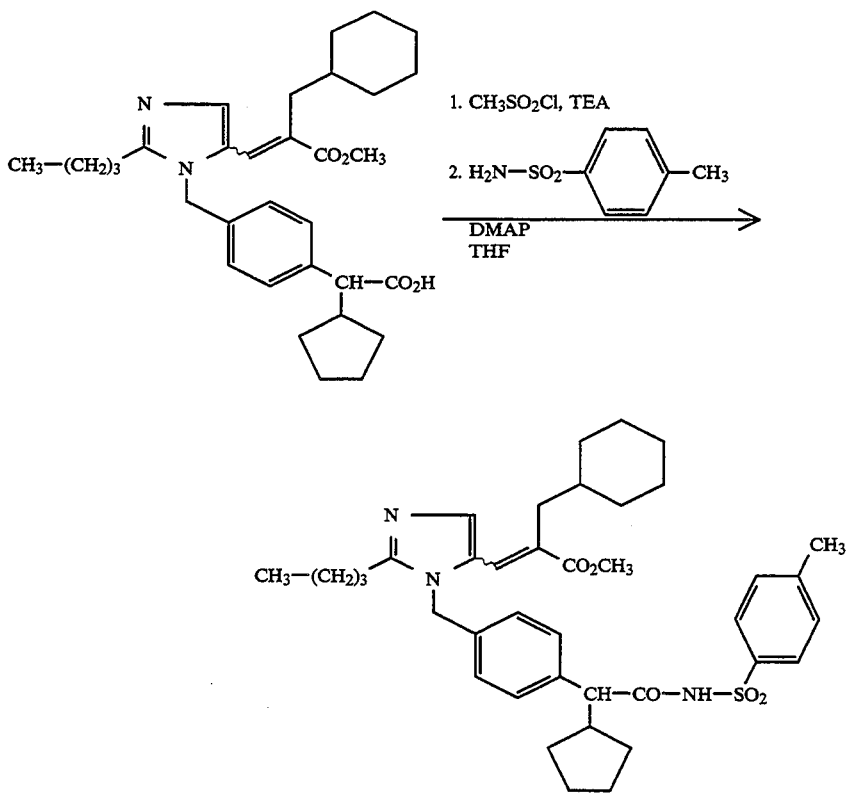

Hydroxyl protective group in the context of the abovementioned definition in general represents a protective group of the series: benzyloxycarbonyl, methanesulphonyl, toluenesulphonyl, 2-nitrobenzyl, 4-nitrobenzyl, 2-nitrobenzyloxycarbonyl, 4-nitrobenzyloxycarbonyl, tert-butoxycarbonyl, allyloxycarbonyl, 4-methoxycarbonyl, acetyl, trichloroacetyl, 2,2,2-trichloroethoxycarbonyl, 2,4-dimethoxybenzyloxycarbonyl, 2-(methylthiomethoxy)ethoxycarbonyl, benzoyl, 4-methylbenzoyl, 4-nitrobenzoyl, 4-fluorobenzoyl, 4-chlorobenzoyl or 4-methoxybenzoyl. Acetyl, methanesulphonyl and toluenesulphonyl are preferred.

Suitable solvents for the process are the customary organic solvents which do not change under the reaction conditions. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoramide, acetonitrile, acetone or nitromethane. It is also possible to use mixtures of the solvents mentioned. Tetrahydrofuran, methylene chloride, toluene and dioxane are preferred for the various steps.

The bases which can be employed for the process according to the invention are in general inorganic or organic bases. These preferably include alkali metal hydroxides or alkaline earth metal hydroxides such as, for example, sodium hydroxide, potassium hydroxide, lithium hydroxide or barium hydroxide, alkali metal carbonates such as sodium carbonate or potassium carbonate, alkaline earth metal carbonates such as calcium carbonate, or alkali metal or alkaline earth metal alkoxides or amides such as sodium methoxide or potassium methoxide, sodium ethoxide or potassium ethoxide or potassium tert-butoxide, or lithium diisopropylamide (LDA), or n-butyllithium or organic amines (trialkyl($C_1C_6$)amines) such as triethylamine or N,N-diisopropylamine, or heterocycles such as 1,4-diazabicyclo[2.2.2]octane (DABCO), 1,8-diazabicyclo[5.4.0]undec-7-ene (DBU), pyridine, N,N-dimethylaminopyridine (DMAP), diaminopyridine, methylpiperidine or morpholine. It is also possible to employ alkali metals (such as sodium) or its hydrides (such as sodium hydride) as bases. Triethylamine, lithium hydroxide, DBU, N,N-dimethylaminopyridine and n-butyllithium are preferred.

In general, the base is employed in an amount from 0.05 mol to 10 mol, preferably from 1 mol to 2 mol, relative to 1 mol of the compound of the formula (III).

The individual steps of the process according to the invention are in general carried out in a temperature range from $-78°$ C. to $+80°$ C., preferably from $-40°$ C. to room temperature. It may be necessary to work under a protective gas atmosphere.

The process according to the invention is in general carried out at normal pressure. However, it is also possible to carry out the process at elevated pressure or at reduced pressure (for example in a range from 0.5 to 5 bar).

The protective group is in general introduced in one of the abovementioned solvents by using a base preferably in methylene chloride using dimethylaminopyridine.

Blocking is in general carried out in a temperature range from $0°$ C. to $+60°$ C., preferably at room temperature and normal pressure.

Elimination is in general carried out in one of the abovementioned solvents, preferably in toluene, and in the presence of one of the abovementioned bases, preferably DBU.

Elimination is in general carried out in a temperature range from +30° C. to +130° C., preferably at +50° C. to +100° C. and at normal pressure.

Suitable bases for hydrolysis are the customary inorganic bases. These preferably include alkali metal hydroxides or alkaline earth metal hydroxides such as, for example, lithium hydroxide, sodium hydroxide, potassium hydroxide or barium hydroxide, or alkali metal carbonates such as sodium carbonate or potassium carbonate or sodium hydrogen carbonate, or alkali metal alkoxides such as sodium methoxide, sodium ethoxide, potassium methoxide, potassium ethoxide or potassium tert-butoxide. Lithium hydroxide, sodium hydroxide or potassium hydroxide are particularly preferred.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide, or dimethyl sulphoxide. Dioxane-water mixtures are particularly preferably employed.

The hydrolysis can also be carried out using acids such as, for example, trifluoroacetic acid (TFA), acetic acid, hydrochloric acid, hydrobromic acid, methanesulphonic acid, sulphuric acid or perchloric acid, preferably using trifluoroacetic acid.

The hydrolysis is in general carried out in a temperature range from 0° C. to +100° C., preferably from +20° C. to +80° C.

In general, the hydrolysis is carried out at normal pressure. However, it is also possible to work at reduced or elevated pressure (for example from 0.5 to 5 bar).

When carrying out the hydrolysis, in general the base is employed in an amount from 1 to 3 mol, preferably from 1 to 1.5 mol, relative to 1 mol of the ester. Molar amounts of the reactants are particularly preferably used.

When carrying out the reaction, the carboxylates of the compounds according to the invention are formed in the first step as intermediates which can be isolated. The acids according to the invention are obtained by treating the carboxylates with customary inorganic acids. These preferably include mineral acids such as, for example, hydrochloric acid, hydrobromic acid, sulphuric acid or phosphoric acid. It has also proved advantageous in this connection in the preparation of the carboxylic acids to acidify the basic reaction mixture from the hydrolysis in a second step without isolation of the carboxylates. The acids can then be isolated in a customary manner.

The amidation and the sulphoamidation are in general carried out in one of the abovementioned solvents, preferably in tetrahydrofuran or dichloromethane.

The amidation and the sulphoamidation can optionally proceed via the activated stage of the acid halides, which can be prepared from the corresponding acids by reaction with thionyl chloride, phosphorus trichloride, phosphorus pentachloride, phosphorus tribromide or oxalyl chloride.

The amidation and the sulphoamidation are in general carried out in a temperature range from −20° C. to +80° C., preferably from −10° C. to +30° C. and at normal pressure.

Suitable bases for this purpose in addition to the abovementioned bases are preferably triethylamine and/or dimethylaminopyridine, DBU, DABCO or N,N-dimethylaminopyridine.

The base is employed in an amount from 0.5 to 10 mol, preferably from 1 mol to 5 mol, relative to 1 mol of the compounds of the general formulae (IV) and (V).

Acid-binding agents for the amidation which can be employed are alkali metal or alkaline earth metal carbonates such as sodium carbonate, potassium carbonate, alkali metal or alkaline earth metal hydroxides such as, for example, sodium hydroxide or potassium hydroxide, or organic bases such as pyridine, triethylamine, N-methylpiperidine, or bicyclic amidines such as 1,5-diazabicyclo[3.4.0]-non-5-ene (DBN) or 1,5-diazabicyclo[3.4.0]undec-5-ene (DBU). Potassium carbonate is preferred.

Suitable dehydrating reagents are carbodiimides such as, for example, diisopropylcarbodiimide, dicyclohexylcarbodiimide or N-(3-dimethylaminopropyl)-N'-ethylcarbodiimide hydrochloride or carbonyl compounds such as carbonyldiimidazole or 1,2-oxazolium compounds such as 2-ethyl-5-phenyl-1,2-oxazolium-3-sulphonate or propanephosphonic anhydride or isobutyl chloroformate or benzotriazolyloxy-tris-(dimethylamino)phosphonium hexafluorophosphate or diphenyl phosphoramidate or methanesulphonyl chloride, if appropriate in the presence of bases such as triethylamine or N-ethylmorpholine or N-methylpiperidine or dicyclohexylcarbodiimide, N-hydroxybenzotriazole or N-hydroxysuccinimide [cf. J. C. Sheehan, S. L. Ledis, J. Am. Chem. Soc. 95, 875 (1973); F. E. Frerman et al., J. Biol. Chem. 258, 7087–7093 (1983) and N. B. Benoton, K. Kluroda, Int. Pept. Prot. Res. 17, 197 (1981)]. N,N-Dicyclohexylcarbodiimide is preferred, if appropriate in the presence of triethylamine and N-hydroxybenzotriazole.

The acid-binding agents and dehydrating reagents are in general employed in an amount from 0.5 to 3 mol, preferably from 1 to 1.5 mol, relative to 1 mol of the corresponding carboxylic acids.

The compounds of the general formula (II) are new and can be prepared by reacting compounds of the general formula (v)

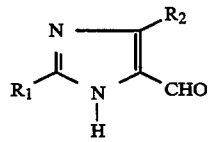

(V)

in which $R^1$ and $R^2$ have the abovementioned meaning, with compounds of the general formula (VI)

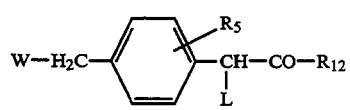

(VI)

in which $R^5$, $R^{12}$ have the abovementioned meaning and w represents halogen, preferably bromine, in one of the abovementioned solvents and in the presence of one of the bases mentioned there, preferably in dimethylformamide using sodium hydride or potassium carbonate.

The compounds of the general formula (III) are known per se or can be prepared by customary methods.

The compounds of the general formula (IV) are new and can be prepared, for example, by the abovementioned process.

The imidazoles of the general formula (V) are known or can be prepared in analogy to processes known from the literature [cf., for example, Bellstein 25, 163; 23 45, U.S. Pat. No. 4,355,040].

The compounds of the general formula (VI) are known in some cases and can be prepared, for example, by alkylating compounds of the general formula (VII)

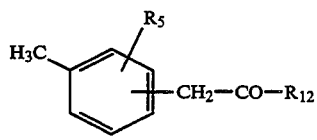

(VII)

in which
R$^5$ and R$^{12}$ have the abovementioned meaning, first with compounds of the general formula (VIII)

L—Z       (VIII)

in which
L has the abovementioned meaning, =and
Z represents halogen, preferably bromine,
in inert solvents, if appropriate in the presence of a base,
and in a second step carrying out a bromination on the methyl group, if appropriate in the presence of a catalyst, according to a customary method.

Alkylation is in general carried out in one of the abovementioned solvents, preferably in dimethylformamide in a temperature range from 0° C. to +70° C., preferably from 0° C. to +30° C. and at normal pressure.

Suitable starters (catalysts) for bromination are, for example, azobisisobutyronitrile, dibenzoyl peroxide, preferably azobisisobutyronitrile, the starter being employed in an amount from 0.01 to 0.1 mol, preferably from 0.01 to 0.05 mol, relative to 1 mol of the compound of the general formula (VI).

The compounds of the general formula (VII) are known per se or can be prepared by known methods [cf. J. Chem. Soc., Perkin Trans. 1, (9), 1706–1707; J. Chem. Soc., Chem. Commun., (2), 167–168].

The compounds of the general formula (VIII) are known per se, [cf. Bellstein 5, 19/5, 24/5, 29] or can be prepared from the corresponding alcohols or cycloalkenes according to a customary method.

The compounds of the general formula (I) according to the invention show an unforeseeable, useful spectrum of pharmacological action.

The compounds according to the invention have a specific A II-antagonistic action, since they inhibit the binding of angiotensin II to A II AT$_1$ receptors, to A II AT$_2$ receptors or to AII AT$_1$ and simultaneously AT$_2$ receptors. They suppress the vasoconstrictor and aldosterone secretion-stimulating effects of angiotensin II. Moreover, they inhibit the proliferation of smooth muscle cells.

They can therefore be employed in medicaments for the treatment of arterial hypertension and atherosclerosis. Moreover, they can be employed for the treatment of coronary heart disease, cardiac insufficiency, brain function disorders, ischaemic brain disease, peripheral circulatory disorders, functional disorders of the kidney and adrenal gland, bronchospastic diseases and diseases of the respiratory tract having a vascular cause, sodium retention and oedemas.

Investigation of the inhibition of the agonist-induced contraction

Rabbits of both sexes are stunned by a blow to the neck and bled out, or in some cases anesthetised with Nembutal (about 60–80 mg/kg i.v.) and sacrificed by opening the thorax. The thorax aorta is taken out, freed from adhering connective tissue, divided into 1.5 mm wide ring segments and individually transferred under an initial loading of about 3.5 g to 10 ml organ baths containing 95% 0$_2$/5% CO$_2$-aerated Krebs-Henseleit nutrient solution temperature-controlled at 37° C. of the following composition: 119 mmol/l of NaCl: 2.5 mmol/l of CaCl$_2 \times$ 2 H$_2$O; 1.2 mmol/l of KH$_2$PO$_4$; 10 mmol/l of glucose; 4.8 mmol/l of KCl; 1.4 mmol/l of MgSO$_4 \times$ 7 H$_2$O and 25 mmol/l of NaHCO$_3$.

The contractions are measured isometrically by Statham UC2 cells by means of bridge amplifiers (ifd Mülheim or DSM Aalen) and digitalised and analysed by means of A/D converters (System 570, Keithley Munich). Agohist dose response curves (DRC) were plotted hourly. With each DRC, 3 or 4 individual concentrations are applied to the baths at an interval of 4 min. After completion of the DRC and subsequent washing-out cycles (16 times, in each case about 5 sec/min with the abovementioned nutrient solution), a 28-minute resting or incubation phase is added in the course of which the contractions usually reach the starting value again.

The height of the 3rd DRC in the normal case is used as a reference quantity for the evaluation of the test substance to be investigated in further passages, which is applied to the baths in the following DRCs in increasing dosage in each case at the start of the incubation time. In this way, each aorta ring is always stimulated for the whole day with the same agohist.

| Agonists and their standard concentrations (Administration volumes per individual dose = 100 μm): | | |
|---|---|---|
| KCL | 22.7; 32.7; 42.7; 52.7 | mmol/l |
| L-Noradrenaline | 3 × 10$^{-9}$; 3 × 10$^{-8}$; 3 × 10$^{-7}$; 3 × 10$^{-6}$ | g/ml |
| Serotonin | 10$^{-8}$; 10$^{-7}$; 10$^{-6}$; 10$^{-5}$ | g/ml |
| B-HT 920 | 10$^{-7}$; 10$^{-6}$; 10$^{-5}$ | g/ml |
| Methoxamine | 10$^{-7}$; 10$^{-6}$; 10$^{-5}$ | g/ml |
| Angiotensin II | 3 × 10$^{-9}$; 10$^{-8}$; 3 × 10$^{-8}$; 10$^{-7}$ | g/ml |

To calculate the IC$_{50}$ (concentration at which the substance to be investigated causes a 50% inhibition), the effect is in each case based on the 3rd=submaximal agonist concentration.

The compounds according to the invention inhibit the contraction of the isolated rabbit aorta induced by angiotensin II in a dose-dependent manner. The contraction induced by potassium depolarisation or other agonists was not inhibited or only weakly inhibited at high concentrations.

Table A

Inhibition of vascular contraction in isolated rabbit aorta rings in vitro $IC_{50}$ (g/ml) against contractions induced by angiotensin II:

| Ex. No.: | $IC_{50}$ [g/ml] |
| --- | --- |
| 4 | $6.3 \times 10^{-8}$ |
| 7 | $5.1 \times 10^{-8}$ |
| 12 | $4.6 \times 10^{-8}$ |

Blood pressure measurements on the angiotensin II-infused rat

Male Wistar rats (Moellegaard, Copenhagen, Denmark) having a body weight of 300–350 g are anaesthetised with Thiopental (100 mg/kg i.p.). After tracheotomy, a catheter for blood pressure measurement is inserted in the femoral artery and a catheter for angiotensin II infusion and a catheter for substance administration are inserted in the femoral veins. After administration of the ganglion blocker pentolinium (5 mg/kg i.v.), the angiotensin II infusion is started (0.3 μg/kg/min). As soon as the blood pressure values have reached a stable plateau, the test substances are administered either intravenously or orally as a suspension or solution in 0.5% Tylose. The blood pressure changes under the effect of the substance are given as average values ±SEM.

Determination of anti-hypertensive activity in conscious hypertensive rats

The oral antihypertensive activity of the compounds according to the invention was tested on conscious rats having a surgically induced unilateral renal artery stenosis. To do this, the right renal artery was constricted with a silver clip of 0.18 mm internal width. In this type of hypertension, the plasma renin activity increases in the first six weeks after intervention. The arterial blood pressure of these animals was measured in a bloodless manner at defined time intervals after substance administration using the "tail cuff". The substances to be tested were administered intragastrally ("orally") by stomach tube at various doses suspended in a Tylose suspension. The compounds according to the invention reduce the arterial blood pressure of the hypertensive rats at a clinically relevant dosage.

Additionally, the compounds according to the invention inhibit the specific binding of radioactive angiotensin II in a concentration-dependent manner.

Interaction of the compounds according to the invention with the angiotensin II receptor on membrane fractions of adrenal gland cortex (bovine)

Bovine adrenal gland cortices (AGC) which have been freshly removed and carefully freed from gland medulla are comminuted in sucrose solution (0.32M) with the aid of an Ultra-turrax (Janke & Kunkel, Staufen I. B.) to give a coarse membrane homogenate and are partially purified to give membrane fractions in two centrifugation steps. The receptor binding investigations are carried out on partially purified membrane fractions of bovine AGC using radioactive angiotensin II in an assay volume of 0.25 ml which, in detail, contains the partially purified membranes (50–80 μg) $^3$H-angiotensin II (3–5 nM), test buffer solution (50 mM tris, pH 7.2), 5 mM $MgCl_2$ and the substances to be investigated. After an incubation time of 60 min at room temperature, the unbound radioactivity of the samples is separated by means of moistened glass fibre filters (Whatman GF/C) and the bound radioactivity is measured spectrophotometrically in a scintillation cocktail after washing the protein with ice-cold buffer solution (50 mM tris/HCl, pH 7.4, 5% PEG 6000). The analysis of the raw data was carried out using computer programs to give $K_i$ or $IC_{50}$ values ($K_i$:$IC_{50}$ values corrected for the radioactivity used; $IC_{50}$ values: concentration at which the substance to be investigated causes a 50% inhibition of the specific binding of the radioligand).

$K_i = 750$ nM      Ex.6

$K_i = 80$ nM      Ex.8

Interaction of the compounds according to the invention with the type 2 angiotensin II receptor ($AT_2$) on membrane fractions of bovine cerebellum For the test, the $AT_2$ receptor "Drug Discovery System" of NEN DuPont (Catalogue No. NED-001) is used. The test is carried out correspondingly using the test protocol additionally supplied. Receptor binding is carried out in a test volume of 235 μl, which in detail contains $^{125}$I-angiotensin II (about 0.1 nM), Test buffer (PBS, NaCl, EDTA, PMSF, DTT, DMSO) and the substances to be investigated. After an incubation of 60 min at 37° C., the unbound radioactivity of the samples is separated by means of moistened glass fibre filters (Whatman GF/C) and the bound radioactivity is measured spectrophotometrically in a scintillation cocktail after washing the protein with ice-cold buffer solution (0.9% strength NaCl). The analysis of the raw data was carried out using computer programs for the $IC_{50}$ or $K_i$ value determination ($IC_{50}$ value: concentration at which the substance to be investigated causes a 50% inhibition of the specific binding of the radioligand: $K_i$ value: $IC_{50}$ value corrected for the radioactivity used).

$K_i(nM) = 827$      Ex. No. 4

Investigation of the inhibition of proliferation of smooth muscle cells by the compounds according to the invention To determine the antiproliferative action of the compounds, smooth muscle cells are used that have been obtained from rats' aortas by the media explant technique [R. Ross, J. Cell. Biol. 50. 172, 1971]. The cells are innoculated into suitable culture dishes (as a rule 96-hole plates, and cultured at 37° C. for 2–3 days in medium containing added serum, 2 mM L-glutamine and 15 mM HEPES, pH 7.4, in 5% $CO_2$. The cells are then synchronised by withdrawal of serum for 2–3 days and then stimulated into growth by serum or other factors. Test desired compounds are added simultaneously. After 16–20 hours, 1 μCi of $^3$H-thymidine is added, and after a further 4 hours, the incorporation of this substance into the TCA-precipitable DNA of the cells is determined.

To determine the halfmaximal inhibition of thymidine incorporation ($IC_{50}$) caused by addition of 10% FCS, the compounds were sequentially diluted in the range of $10^{-6}$M to $10^{-9}$M.

| Ex. No. | % Inhibition at $10^{-6}$ M |
| --- | --- |
| 5 | 90 |

The new active compounds can be converted in a known manner into the customary formulations, such as tablets, coated tablets, pills, granules, aerosols, syrups, emulsions, suspensions and solutions, using inert, non-toxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can optionally be used as auxiliary solvents.

Administration is carried out in a customary manner, preferably orally or parenterally, in particular perlingually or intravenously.

In the case of parenteral administration, solutions of the active compound can be employed using suitable liquid excipient materials.

In general, it has proved advantageous on intravenous administration to administer amounts of about 0.001 to 1 mg/kg, preferably about 0.01 to 0.5 mg/kg of body weight to achieve effective results, and on oral administration the dosage is about 0.01 to 20 mg/kg, preferably 0.1 to 10 mg/kg of body weight.

In spite of this, it may be necessary to deviate from the amounts mentioned, in particular depending on the body weight or the type of administration route, on individual behaviour towards the medicament, the manner of its formulation and the time or interval at which administration takes place. Thus, in some cases it may be adequate to manage with less than the abovementioned minimum amount, while in other cases the upper limit mentioned must be exceeded. In the case of the administration of relatively large amounts, it may be advisable to divide these into several individual doses over the course of the day.

Solvent mixtures

A: Ethyl acetate/petroleum ether 40–60=7:3
B: Dichloromethane/methanol=9:1
C: Dichloromethane/methanol/glacial acetic acid=9:1:0.1
D: Ethyl acetate/petroleum ether 40–60=1:1
Toluene/ethyl acetate =1:3

Starting Compounds

Example I

Tert-butyl 2- [4-{2-n-butyl-4-chloro-5-(1-(3-cyclohexyl-1-hydroxy-2-methoxycarbonyl)propyl)-1H-imidazol-1-yl -methyl}phenyl]-2-cyclopentyl-acetate

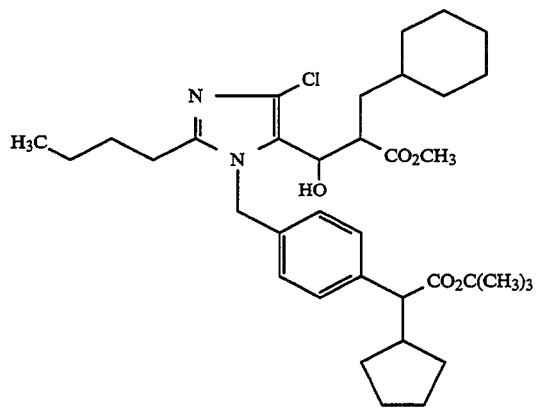

25.9 ml of a 1.6N solution (41.4 mmol) of n-butyllithium in n-hexane are added dropwise with stirring at −78° C. under argon to a solution of 4.4 g (44 mmol) of diisopropylamine in 50 ml of tetrahydrofuran. After warming to 0° C. for 5 minutes, the mixture is again cooled to −78° C. and a solution of 6.4 g (37.7 mmol) of methyl 3-cyclohexyl-propionate in 25 ml of tetrahydrofuran is added dropwise such that the temperature does not exceed −60° C. The mixture is stirred at −78° C. for a further 30 minutes and a solution of 11.5 g (25.1 mmol) of tert-butyl 2-[4-(2-n-butyl-4-chloro-5-formyl-imidazol-1-yl-methyl)phenyl]-2-cyclopentyl-acetate in 25 ml of tetrahydrofuran is then in turn added dropwise such that the temperature does not exceed −60° C. After 45 minutes at −78° C., the mixture is allowed to thaw and is treated with 20 ml of aqueous ammonium chloride solution. After three times extraction with ethyl acetate, the combined organic phases are dried over sodium sulphate, filtered and concentrated, and the residue is chromatographed on silica gel 60 using petroleum ether 40–60/ethyl acetate=6:1.

Yield: 11.2 g (74% of theory) $R_f$=0.72/0.83 (petroleum ether 40–60/ethyl acetate=1:1)

Example II

Tert-butyl 2-[4-{2-n-butyl-4-chloro-5-(1-(1-acetoxy-3-cyclohexyl-2-methoxycarbonyl)propyl)-1H-imidazol-1-yl-methyl}phenyl]-2-cyclopentyl-acetate

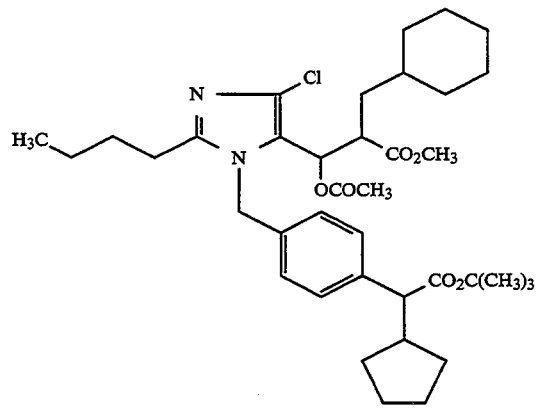

A solution of 11.0 g (17.5 mmol) of the compound from Example I in 300 ml of dichloromethane is treated with 0.9 g (7.2 mmol) of N,N-dimethylaminopyridine and 1.8 g (18.3 mmol) of acetic anhydride and the mixture is stirred at room temperature for 3 hours. After addition of diethyl ether, the organic phase is shaken with water, aqueous bicarbonate solution, aqueous sodium chloride solution and again with water, separated off, dried over sodium sulphate, filtered and concentrated.

Yield: 11.3 g (97% of theory) $R_f$=0.84 (petroleum ether 40–60/ethyl acetate=5:4)

Preparation Example

Example 1 and Example 2 tert-Butyl (E)-2-[4-{2-n-butyl-4-chloro-5-(1-(3-cyclohexyl-2-methoxycarbonyl)-prop-1-en-yl)-1H-imidazol-1-yl-methyl}phenyl]-2-cyclopentyl-acetate

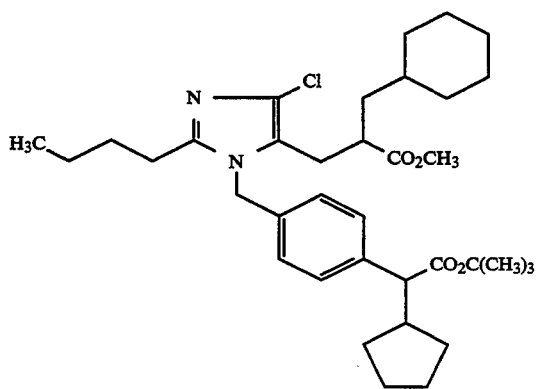

tert-Butyl (Z)-2-[4-{2-n-butyl-4-chloro-5-(1-(3-cyclohexyl-2-methoxycarbonyl)-prop-1-en-yl)-1H-imidazol-1-yl-methyl}phenyl]-2-cyclopentyl-acetate (Example 2)

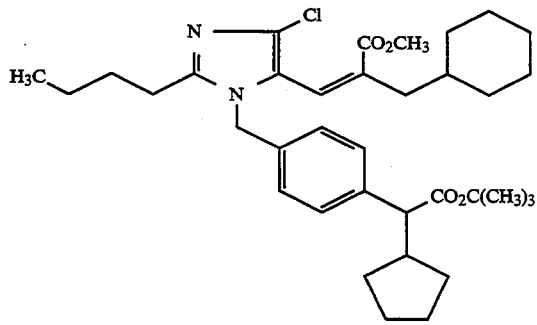

11.2 g (16.7 mmol) of the compound from Example 2 are dissolved in 130 ml of toluene, and the solution is treated at room temperature with 6.4 g (41.9 mmol) of 1,8-diazabicyclo[5.4.0]undec-7-ene and stirred at 80° C. for 18 hours. After a fresh addition of the see amount of base and stirring at 80° C. for a further 10 h, the mixture is cooled, diluted with toluene and shaken with aqueous sodium chloride solution. The organic phase is separated off, dried over sodium sulphate, filtered and concentrated and the residue is chromatographed on silica gel 60 using petroleum ether 40–60/ethyl acetate (4:1).

Example 1: yield: 4.5 g (44% of theory)

Example 1: $R_f$=0.35 (petroleum ether 40–60/ethyl acetate=4:1)

Example 2: yield: 1.2 g (11% of theory)

Example 2: $R_f$=0.21 (petroleum ether 40–60/ethyl acetate=4:1)

Example 3

(E)-2-[4-{2-n-Butyl-4-chloro-5-(1-(3-cyclohexyl-2-methoxycarbonyl)-prop-1-en-yl)-1H-imidazol-1-yl-methyl}phenyl]-2 -cyclopentyl-acetic acid

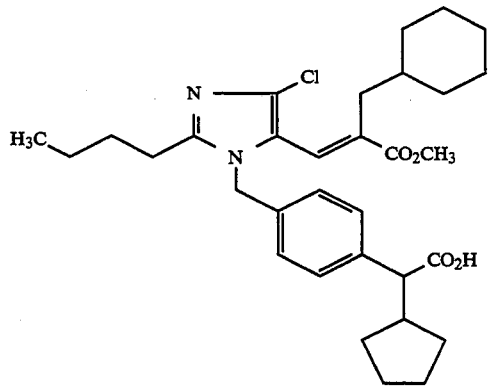

A solution of 4.4 g (7.2 mmol) of the compound from Example 1 in 20 ml of dichloromethane is stirred at room temperature with 20 ml of trifluoroacetic acid for 4 hours. It is then rendered alkaline with aqueous bicarbonate solution, treated with diethyl ether, adjusted to pH 2 with aqueous 1N HCl extracted by shaking and separated. After again extracting the aqueous phase twice with ethyl acetate, the combined organic phases are dried over sodium sulphate, filtered and concentrated.

Yield: 3.9 g (98% of theory) $R_f$=0.49 (dichloromethane/methanol/glacial acetic acid=9:1:0.1)

Example 4

(E)-2-[4-{2-n-Butyl -4-chloro-5-(1-(2-carboxy-3-cyclohexyl-prop-1-en-yl)-1H-imidazol-1-yl-methyl} phenyl]-2-cyclopentyl-acetic acid

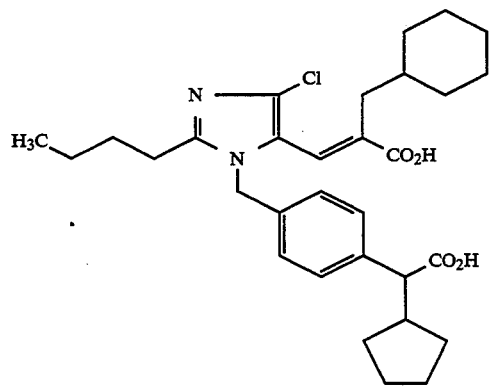

A solution of 300 mg (0.5 mmol) of the compound from Example 3 in 20 ml of dioxane/water (1:1) is treated at room temperature with a solution of 50 mg (1.2 mmol) of lithium hydroxide in 6 ml of water and the mixture is stirred at room temperature for 18 hours. It is then concentrated, diluted with water and extracted with diethyl ether. The aqueous phase is acidified with 1N HCl, extracted three times with ethyl acetate, and the combined ethyl acetate phases are dried over sodium sulphate, filtered and concentrated.

Example 5

(E)-2-[4-{2-n-Butyl-4-chloro-5-(3-cyclohexyl-2-methoxyarbonyl-prop-1-en-yl)-1H-imidazol-1-methyl}phenyl]-2-cyclopentyl-acetic acid L-phenylglycinolamide

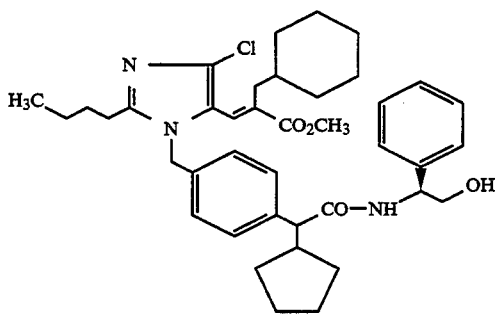

A solution of 1.2 g (2.2 mmol) of the compound from Example 3 in 40 ml of dichloromethane is treated at room temperature under argon with 0.51 g (3.3 mmol) of 1-hydroxy-1H-benzotriazole, cooled to 0° C. and, after addition of 0.44 g (4.4 mmol) of triethylamine and 0.68 g (3.3 mmol) of N,N′-dicyclohexylcarbodiimide, stirred for 30 minutes. A solution of 0.36 g (2.6 mmol) of L-phenylglycinol in 20 ml of dichloromethane is then added dropwise. After stirring for 1 hour, the mixture is slowly warmed to room temperature and stirred overnight. For working-up, it is treated with water and extracted three times with dichloromethane. The combined organic phases are dried over sodium sulphate, filtered and chromatographed on silica gel 60 using toluene/ethyl acetate (1:1)

Yield=1.13 g (76% of theory) $R_f$=0.50/0.55 (dichloromethane/methanol 9:1)

Example 6

(E)-N-4-Toluenesulphonyl-2-[4-{2-n-butyl-4-chloro-5-(3-cyclohexyl-2-methoxycarbonyl-prop-1-en-yl)-1H-imidazol-1-yl-methyl}phenyl]-2-cyclopentyl-acetamide

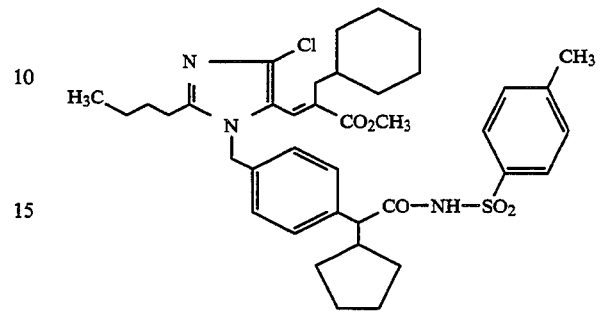

A solution of 1.2 g (2.2 mmol) of the compound from Example 3 in 40 ml of tetrahydrofuran is treated at −30° C. under argon with 0.44 g (4.4 mmol) of triethylamine and 0.28 g (2.4 mmol) of methanesulphonyl chloride and the mixture is stirred for 2 hours. A solution of 0.45 g (2.6 mmol) of p-toluenesulphonamide and 0.29 g (2.2 mmol) of N,N-dimethylaminopyridine in 20 ml of tetrahydrofuran is then added dropwise, and the mixture is stirred for a further 1 hour, slowly allowed to come to room temperature and stirred overnight. For working-up, it is treated with 10 ml of 1N acetic acid and extracted three times with ethyl acetate. The combined organic phases are dried over sodium sulphate, filtered and concentrated and the residue is chromatographed on silica gel 60 using toluene/ethyl acetate (1:3).

Yield: 0.82 g (55% of theory) $R_f$=0.83 (ethyl acetate/petroleum ether 40:60=7:3)

The examples shown in Tables 1 and 2 are prepared in analogy to the examples given there:

TABLE 1

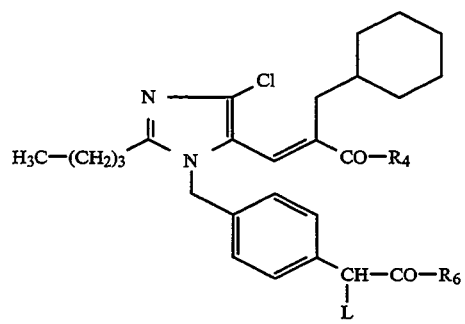

(E)

| Ex. No. | L | R⁴ | R⁶ | Isomer | In analogy to the procedure of example | $R_f$(eluent) |
|---|---|---|---|---|---|---|
| 7 | cyclopentyl | —OH | —NH—SO₂—C₆H₄—CH₃ | rac | 6/4 | 0.40 C |
| 8 | cyclopentyl | —OH | —NH—CH(C₆H₅)—CH₂OH | dia | 5/4 | 0.39 C |
| 9 | —CH₂—C₆H₅ | —OH | OH | rac | 4 | 0.27 B |

TABLE 1-continued (E)

Structure: imidazole with H3C—(CH2)3 at 2-position, Cl at 5-position, cyclohexylmethyl-substituted acrylate (=CH—C(CO—R4)=CH—cyclohexyl) at 4-position, and N-benzyl where the para position of benzyl bears —CH(L)—CO—R6.

| Ex. No. | L | R⁴ | R⁶ | Isomer | In analogy to the procedure of example | R_f (eluent) |
|---|---|---|---|---|---|---|
| 10 | —CH₂C₆H₅ | —OH | —NH—SO₂—C₆H₄—CH₃ | rac | 6/4 | 0.45 B |
| 11 | —CH₂C₆H₅ | —OH | —NH—CH(C₆H₅)—CH₂OH | dia | 5/4 | 0.40 B |
| 12 | cycloheptyl | —OH | OH | rac | 4 | 0.33 B |
| 13 | —CH(CH₃)₂ | —OH | —OH | rac | 4 | 0.44 C |
| 14 | —CH(CH₃)₂ | —OCH₃ | —NH—CH(C₆H₅)—CH₂OH | dia A | 5 | 0.46 D |
| 15 | —CH(CH₃)₂ | —OCH₃ | —NH—CH(C₆H₅)—CH₂OH | dia B | 5 | 0.35 D |
| 16 | —CH(CH₃)₂ | —OH | —NH—CH(C₆H₅)—CH₂OH | dia A | 5/4 | 0.26 B |
| 17 | —CH(CH₃)₂ | —OH | —NH—CH(C₆H₅)—CH₂OH | dia B | 5/4 | 0.37 B |
| 18 | —CH(CH₃)₂ | —OH | —NHSO₂—C₆H₄—CH₃ | rac | 6/4 | 0.43 B |

TABLE 2
(Z)
| Ex. No. | L | R⁴ | R⁶ | Isomer | In analogy to the procedure of example | $R_f$(eluent) |
|---|---|---|---|---|---|---|
| 19 | —CH(CH₃)₂ | —OH | OH | rac | 4 | 0.47 C |
| 20 | —CH₂C₆H₅ | —OH | OH | dia | 4 | 0.45 C |
| 21 |  | —OH | OH | rac | 4 | 0.44 C |
| 22 |  | —OH | OH | rac | 4 | 0.44 C |
| 23 | 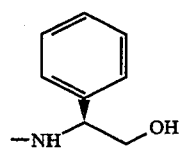 | —OCH₃ |  | dia | 5 | 0.74/0.70 A |
| 24 | 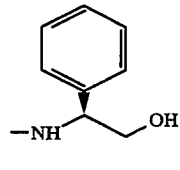 | —OCH₃ |  | dia | 5 | 0.72 A |
| 25 | 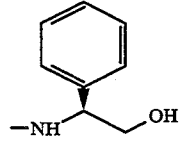 | —OH |  | dia | 5/4 | 0.08 A |
| 26 | 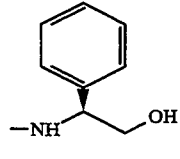 | —OH |  | dia | 5/4 | 0.12 A |
| 27 | 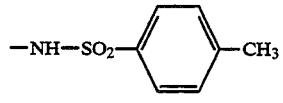 | —OH | —NH—SO₂—⟨C₆H₄⟩—CH₃ | rac | 6/4 | 0.47 B |

TABLE 2-continued

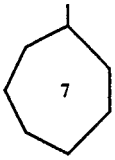

(Z)

| Ex. No. | L | $R^4$ | $R^6$ | Isomer | In analogy to the procedure of example | $R_f$(eluent) |
|---|---|---|---|---|---|---|
| 28 | 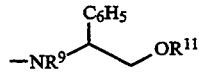 | —OH | —NH—SO$_2$—⟨C$_6$H$_4$⟩—CH$_3$ | rac | 6/4 | 0.46 B |

We claim:

1. A propenoyl-imidazole of the formula

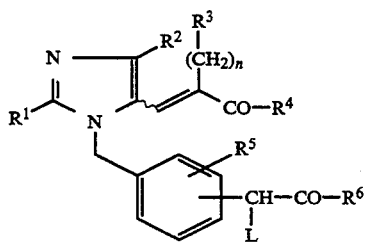

in which $R^1$ represents straight-chain or branched alkyl or alkenyl each having up to 8 carbon atoms, or represents cycloalkyl having 3 to 8 carbon atoms, $R^2$ represents hydrogen, halogen or perfluoroalkyl having up to 5 carbon atoms, n represents a number 0, 1, 2 or 3, $R^3$ represents cycloalkyl having 3 to 7 carbon atoms, $R^4$ represents hydroxyl, or straight-chain or branched alkoxy having up to 6 carbon atoms, or represents a radical of the formula —CO—NR$^7$R$^8$, in which $R^7$ and $R^8$ are identical or different and denote hydrogen, straight-chain or branched alkyl having up to 6 carbon atoms or phenyl, $R^5$ represents hydrogen, halogen, nitro, hydroxyl, trifluoromethyl, trifluoromethoxy, straight-chain or branched alkyl, alkoxy or alkoxycarbonyl, each having up to 6 carbon atoms, cyano or carboxyl, L represents cycloalkyl having 3 to 7 carbon atoms, or represents straight-chain or branched alkyl having up to 8 carbon atoms, which is optionally substituted by phenyl, $R^6$ represents hydroxyl or straight-chain or branched alkoxy having up to 6 carbon atoms, or represents a radical of the formula —NR$^9$SO$_2$R$^{10}$ or

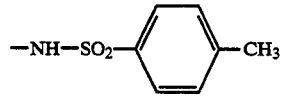

in which $R^9$ denotes hydrogen or straight-chain or branched alkyl having up to 4 carbon atoms, $R^{10}$ denotes straight-chain or branched alkyl having up to 6 carbon atoms or phenyl which is optionally substituted by straight-chain or branched alkyl having up to 6 carbon atoms, $R^{11}$ denotes hydrogen, straight-chain or branched alkyl having up to 6 carbon atoms or a hydroxyl-protective group selected from the group consisting of benzyloxycarbonyl, methanesulphonyl, toluenesulphonyl, 2-nitrobenzyloxycarbonyl, tert-butoxycarbonyl, allyloxycarbonyl, 4-methoxycarbonyl, acetyl, trichloroacetyl, 2,2,2-trichloroethoxycarbonyl, 2,4-dimethoxybenzylcarbonyl, 2-(methylthiomethoxy)ethoxycarbonyl, benzoyl, 4-methylbenzoyl, 4-nitrobenzoyl, 4-fluorobenzoyl, 4-chlorobenzoyl and 4-methoxybenzoyl, or a salt thereof.

2. A propenoyl-imidazole according to claim 1, in which $R^1$ represents straight-chain or branched alkyl or alkenyl each having up to 6 carbon atoms, or represents cyclopropyl, cyclobutyl, cyclopentyl, cyclohexyl or cycloheptyl, $R^2$ represents hydrogen, fluorine, chlorine, bromine or perfluoroalkyl having up to 4 carbon atoms, n represents a number 0, 1 or 2, $R^3$ represents cyclopropyl, cyclobutyl, cyclopentyl, cyclohexyl or cycloheptyl, $R^4$ represents hydroxyl, straight-chain or branched alkoxy having up to 4 carbon atoms, or represents the group of the formula —CO—NR$^7$R$^8$, in which $R^7$ and $R^8$ are identical or different and denote hydrogen, straight-chain or branched alkyl having up to 4 carbon atoms or phenyl, $R^5$ represents hydrogen, fluorine, chlorine, bromine, trifluoromethyl, carboxyl or straight-chain or branched alkyl, alkoxy or alkoxycarbonyl each having up to 4 carbon atoms, L represents cyclopropyl, cyclobutyl, cyclopentyl, cyclohexyl or cycloheptyl, or represents straight-chain or branched alkyl having up to 6 carbon atoms or benzyl, R⁶ represents hydroxyl or straight-chain or branched alkoxy having up to 4 carbon atoms, or represents a radical of the formula —NR⁹SO₂R¹⁰ or

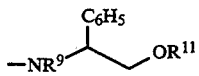

in which

R⁹ denotes hydrogen, methyl or ethyl,
R¹⁰ denotes straight-chain or branched alkyl having up to 4 carbon atoms or phenyl which is optionally substituted by straight-chain or branched alkyl having up to 4 carbon atoms,
R¹¹ denotes hydrogen, straight-chain or branched alkyl having up to 4 carbon atoms, acetyl or benzyl, or a salt thereof.

3. A propenoyl-imidazole according to claim 1, in which

R¹ represents straight-chain or branched alkyl or alkenyl, each having up to 4 carbon atoms, or represents cyclopropyl, cyclopentyl or cyclohexyl,
R² represents hydrogen, fluorine, chlorine or perfluoroalkyl having up to 2 carbon atoms,
n represents the number 0 or 1,
R³ represents cyclopentyl or cyclohexyl,
R⁴ represents hydroxyl, methoxy, ethoxy or tert-butoxy,
R⁵ represents hydrogen, fluorine, chlorine, bromine, trifluoromethyl, trifluoromethoxy or methyl,
L represents cyclopentyl, cyclohexyl or cycloheptyl, or represents straight-chain or branched alkyl having up to 4 carbon atoms or benzyl,
R⁶ represents hydroxyl or straight-chain or branched alkoxy having up to 4 carbon atoms, or represents a radical of the formula —NR⁹SO₂R¹⁰ or

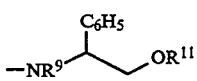

in which

R⁹ denotes hydrogen or methyl,
R¹⁰ denotes methyl or p-tolyl,
R¹¹ denotes hydrogen or straight-chain or branched alkyl having up to 3 carbon atoms or benzyl, or a salt thereof.

4. A propenoyl-imidazole according to claim 1 in which the radical —CH(L)—CO—R⁴ is in the para-position to the imidazolylmethyl group.

5. A compound according to claim 1 wherein such compound is 2-[4-{2-n-butyl-4-chloro-5-(3-cyclohexyl-2-methoxycarbonyl-prop-1-en-yl)-1-H-imidazol-1-methyl}phenyl]-2-cyclopentyl-acetic acid-4L-phenyl glycinolamide of the formula

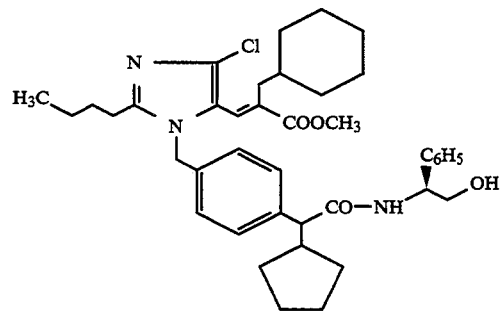

or a salt thereof.

6. A compound according to claim 1 wherein such compound is N-4-toluenesulphonyl-2-[4-{2-n-butyl-4-chloro-5-(3-cyclohexyl-2-carboxy-prop-1-en-yl)-1H-imidazol-1-yl-methyl}phenyl]-2-cyclopentyl-acetamide of the formula

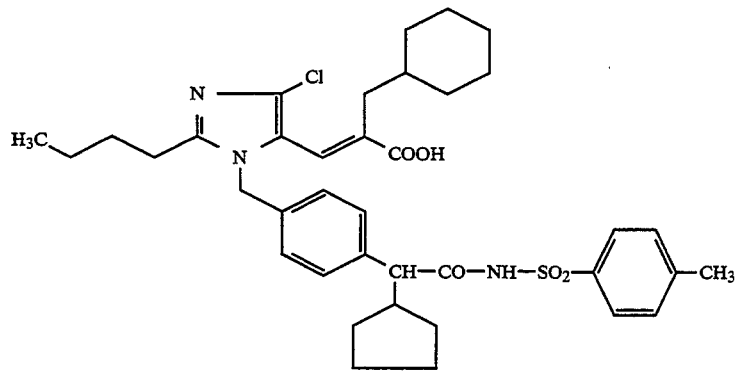

or a salt thereof.

7. A compound according to claim 1 wherein such compound is 2-[4-{2-n-butyl-4-chloro-5-(3-cyclohexyl-2-carboxy-prop-1-en-yl)-1H-imidazol-1-yl-methyl}]-2-isopropyl-acetic acid-L-phenyl-glycinol amide of the formula 8. A compound according to claim 1 wherein such compound is 2-[4-{2-n-butyl-4-chloro-5-(3-cyclohexyl- 2-carboxy-prop-1-en-yl)-1H-imidazol-1-yl-methyl}
phenyl]-2-cycloheptyl-acetic acid of the formula

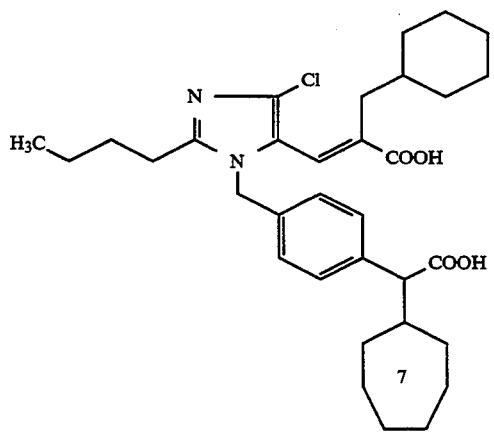

or a salt thereof.

9. A compound according to claim 1 wherein such compound is 2-[4-{2-n-butyl-4-chloro-5-(3-cyclohexyl-2-methoxy-carbonyl-prop-1 -en-yl)-1H-imidazol-1-yl -methyl}phenyl]-2-cycloheptyl-acetic acid-L-phenyl-glycinol amide of the formula

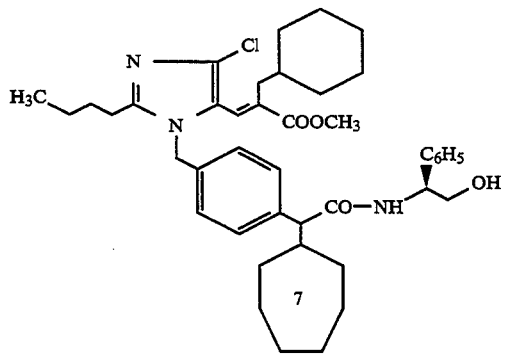

or a salt thereof.

10. A composition for the treatment of atriable hypertension and arteriosclerosis comprising an amount effective therefor of a compound or salt thereof according to claim 1 and a pharmacologically acceptable diluent.

11. The method of treating atriable hypertension and arteriosclerosis in a patient in need thereof which comprises administering to such patient an amount effective therefor of a compound or salt thereof according to claim 1.

* * * * *